US010436011B2

United States Patent
Wu et al.

(10) Patent No.: US 10,436,011 B2
(45) Date of Patent: Oct. 8, 2019

(54) MULTI-STRING MONITORING USING ELECTRO-MAGNETIC (EM) CORROSION DETECTION TOOL

(71) Applicant: HALLIBURTON ENERGY SERVICES, INC., Houston, TX (US)

(72) Inventors: Dagang Wu, Katy, TX (US); Burkay Donderici, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 202 days.

(21) Appl. No.: 15/118,466

(22) PCT Filed: Apr. 7, 2015

(86) PCT No.: PCT/US2015/024688
§ 371 (c)(1),
(2) Date: Aug. 11, 2016

(87) PCT Pub. No.: WO2015/157268
PCT Pub. Date: Oct. 15, 2015

(65) Prior Publication Data
US 2017/0167241 A1  Jun. 15, 2017

Related U.S. Application Data

(60) Provisional application No. 61/978,126, filed on Apr. 10, 2014.

(51) Int. Cl.
*E21B 47/00* (2012.01)
*G01V 3/30* (2006.01)
(Continued)

(52) U.S. Cl.
CPC ............ *E21B 47/00* (2013.01); *G01N 27/02* (2013.01); *G01V 3/30* (2013.01); *G01V 3/34* (2013.01); *G01V 3/38* (2013.01)

(58) Field of Classification Search
None
See application file for complete search history.

(56) References Cited

U.S. PATENT DOCUMENTS

2005/0156602 A1   7/2005   Conti
2010/0194584 A1   8/2010   Savage
(Continued)

FOREIGN PATENT DOCUMENTS

WO   2015/157268   10/2015

OTHER PUBLICATIONS

"Successful Application of a New Electromagnetic Corrosion Tool for Well Integrity Evaluation in Old Wells Completed with Reduced Diameter Tubular", by Garcia et al. Presented Mar. 26-28, 2013. IPTC 16997.

(Continued)

*Primary Examiner* — Roy Y Yi
*Assistant Examiner* — Geoffrey T Evans
(74) *Attorney, Agent, or Firm* — Benjamin Fite; C. Tumey Law Group PLLC (57) ABSTRACT

A multi-string corrosion monitoring method includes using a first set of electromagnetic (EM) log data to calculate attributes of a first casing string while attributes of a second casing string are assigned a fixed value. The method also includes using a second set of EM log data to calculate attributes of a second casing string while attributes of the first casing string are assigned a fixed value.

19 Claims, 5 Drawing Sheets

(51) Int. Cl.
*G01N 27/02* (2006.01)
*G01V 3/34* (2006.01)
*G01V 3/38* (2006.01)

(56) References Cited

U.S. PATENT DOCUMENTS

| | | |
|---|---|---|
| 2010/0206064 A1 | 8/2010 | Estes |
| 2012/0024050 A1 | 2/2012 | Godager |
| 2013/0000906 A1 | 1/2013 | Schultz et al. |
| 2013/0193953 A1 | 8/2013 | Yarbro et al. |
| 2014/0067272 A1* | 3/2014 | San Martin .............. G01V 3/28 702/7 |

OTHER PUBLICATIONS

"Electromagnetic Casing Inspection Tool for Corrosion Evaluation" by Brill et al., Presented Feb. 7-9, 2012. IPTC14865.
Extended European Search Report for Application No. 15777010. 8-1609/3129587 PCT/US2015024688 dated Nov. 21, 2017.
Acuna, Alexandra Irlec et al., "Scanning for Downhole Corrosion", "Applying Electrical Micro-Imaging Logs to Reservoir Characterization" *Oilfield Review* 22, No. 1 (2010): 42-50.
Rourke, M., et al., "Multi-tubular Corrosion Inspection Using a Pulsed Eddy Current", IPTC 16645, Mar. 26-28, 2013, 6 pgs.
PCT International Search Report & Written Opinion, dated Jul. 22, 2015, Appl No. PCT/US2015/024688, "Multi-string Monitoring Using Electromagnetic (EM) Corrosion Detection Tool," filed Apr. 7, 2015, 16 pgs.

* cited by examiner

FIG. 5B

MULTI-STRING MONITORING USING ELECTRO-MAGNETIC (EM) CORROSION DETECTION TOOL

CROSS-REFERENCE TO RELATED APPLICATIONS

The present application claims priority to U.S. Pat. App. 61/978,126 titled "Multi-String Monitoring Using Electromagnetic (EM) Corrosion Detection Tool", filed Apr. 10, 2014 by inventors Dagang Wu and Burkay Donderici, which is incorporated by reference in its entirety.

BACKGROUND

For oil and gas exploration and production, a network of wells installations and other conduits are established by connecting sections of metal pipe together. For example, a well installation may be completed, in part, by lowering multiple sections of metal pipe (i.e., a casing string) into a borehole, and cementing the casing string in place. In some well installations, multiple casing strings are employed (e.g., a concentric multi-string arrangement) to allow for different operations related to well completion, production, or enhanced oil recovery (EOR) options.

Corrosion of metal pipes is an ongoing issue. Efforts to mitigate corrosion include use of corrosion-resistant alloys, coatings, treatments, corrosion transfer, etc. Also, efforts to improve corrosion monitoring are ongoing. For downhole casing strings, various types of corrosion monitoring tools are available. One type of corrosion detection tool uses electromagnetic (EM) fields to estimate pipe thickness or other corrosion indicators. As an example, an EM logging tool may collect EM log data, where the EM log data can be interpreted to correlate a level of flux leakage or EM induction with corrosion. When multiple casing strings are employed together, correctly managing corrosion detection EM logging tool operations and data interpretation is not a trivial task.

BRIEF DESCRIPTION OF THE DRAWINGS

Accordingly, there are disclosed in the drawings and the following description various an electromagnetic (EM) logging tool for multi-string corrosion monitoring and related methods. In the drawings.

It should be understood, however, that the specific embodiments given in the drawings and detailed description do not limit the disclosure. On the contrary, they provide the foundation for one of ordinary skill to discern the alternative forms, equivalents, and modifications that are encompassed together with one or more of the given embodiments in the scope of the appended claims.

DETAILED DESCRIPTION

Disclosed herein is an electromagnetic (EM) logging tool for multi-string corrosion monitoring and related methods. To distinguish between different casing strings in a multi-string scenario, the EM logging tool employs different components or different operations for each casing string. For example, the EM logging tool may include different sensor arrays to enable collection of EM log data that corresponds to different casing strings. As another option, the EM logging tool may employ different frequency channels to enable collection of EM log data that corresponds to different casing strings. As another option, the EM logging tool may employ different time channels to enable collection of EM log data that corresponds to different casing strings.

Once EM log data corresponding to different casing strings is collected, it is processed. The processing of EM log data may be performed downhole and/or at earth's surface to derive attributes (e.g., casing thickness, casing conductivity, and/or casing permeability) for each of multiple casing strings as a function of depth. The derived attributes can further be correlated with one or more types of corrosion and/or with a corrosion index. If corrosion of a particular casing string is determined to exceed a threshold, a corrective action may be performed. Example corrective actions include enhancing, repairing, or replacing at least part of a casing segment. Additionally or alternatively, a treatment can be applied to reduce the rate of corrosion for at least part of a casing segment.

In at least some embodiments, the processing of EM log data involves a multi-stage inversion. For example, a first stage of inversion may involve inverting based on a first set of EM log data to determine attributes of a first casing string while attributes of a second casing string are assigned a fixed value. Meanwhile, a second stage of inversion may involve inverting based on a second set of EM log data to determine attributes of a second casing string while attributes of the first casing string are assigned a fixed value. Further, each stage of inversion may include multiple levels. As an example, a first level may involve determining casing thickness while assigning a fixed value to the casing conductivity and permeability. Meanwhile, a second level may involve determining a solution for the casing conductivity and/or permeability while the casing thickness is assigned a fixed value. For attribute calculations (with or without the multi-stage inversion), multiple iterations may be performed until a threshold accuracy and/or threshold number of iterations is reached. Various EM logging tool options and EM log data processing options related to multi-string monitoring are disclosed herein.

Figure 1A:
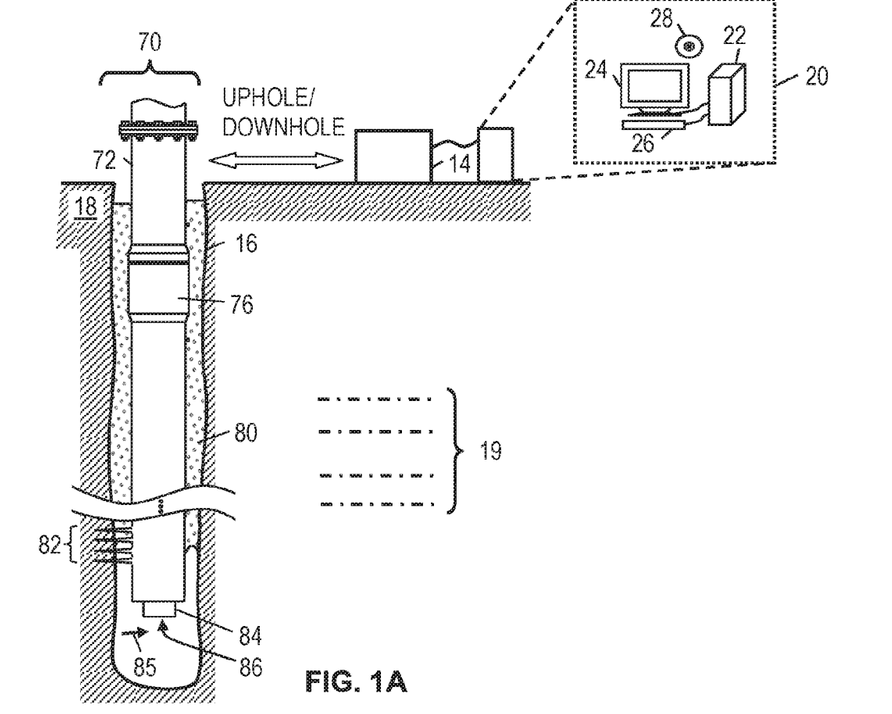
FIGS. 1A and 1B depict various illustrative multi-string survey environments.
Figure 1B:
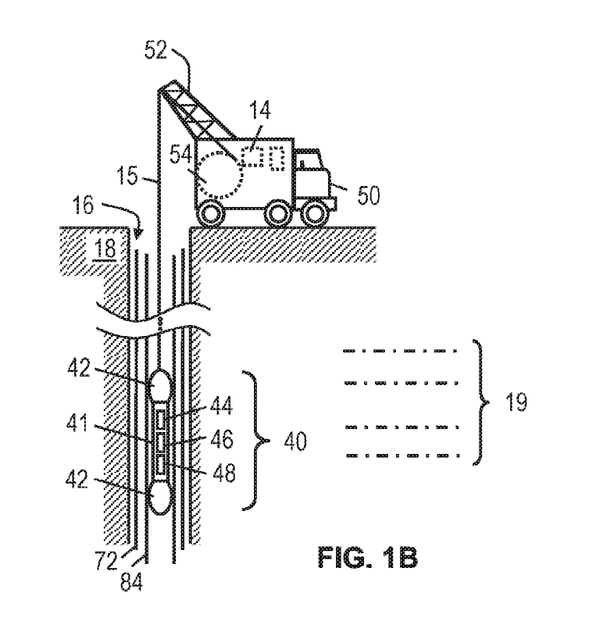

To provide some context for the disclosure, FIGS. 1A and 1B show illustrative multi-string survey environments. FIG. 1A shows a permanent well survey environment, where a drilling rig has been used to drill borehole 16 that penetrates formations 19 of the earth 18 in a typical manner. Further, a casing string 72 is positioned in the borehole 16. The casing string 72 of well 70 includes multiple tubular casing sections (usually about 30 feet long) connected end-to-end by couplings 76. It should be noted that FIG. 1A is not to scale, and that casing string 72 typically includes many such couplings 76. Further, the well 70 includes cement slurry 80 that has been injected into the annular space between the outer surface of the casing string 72 and the inner surface of the borehole 16 and allowed to set. Further, a production tubing string 84 has been positioned in an inner bore of the casing string 72. Both the casing string 72 and the production tubing string 84 are formed from multiple segments of metal pipe and are subject to corrosion.

In FIG. 1A, the well 70 corresponds to a production well and is adapted to guide a desired fluid (e.g., oil or gas) from a bottom of the borehole 16 to a surface of the earth 18.

Accordingly, perforations 82 may be formed at a bottom of the borehole 16 to facilitate the flow of a fluid 85 from a surrounding formation into the borehole 16 and thence to earth's surface via an opening 86 at the bottom of the production tubing string 84. Note that well configuration of FIG. 1A is illustrative and not limiting on the scope of the disclosure. Other examples of permanent well installations include injection wells and monitoring wells. Further, well 70 may include other casing strings in addition to or instead of casing string 72 and production tubing string 84.

In the multi-string EM field survey environment of FIG. 1A, uplink or downlink information is transferred between an EM logging tool (see e.g., FIG. 1B) and a surface interface 14 and/or computer system 20. In some embodiments, the surface interface 14 and/or the computer system 20 may perform various operations such as converting signals from one format to another, storing EM log data collected by an EM logging tool, and/or processing EM log data to determine casing string attributes as described herein. In at least some embodiments, the computer system 20 includes a processing unit 22 that performs the EM log data analysis operations by executing software or instructions obtained from a local or remote non-transitory computer-readable medium 28. The computer system 20 also may include input device(s) 26 (e.g., a keyboard, mouse, touchpad, etc.) and output device(s) 24 (e.g., a monitor, printer, etc.). Such input device(s) 26 and/or output device(s) 24 provide a user interface that enables an operator to interact with an EM logging tool and/or software executed by the processing unit 22. For example, the computer system 20 may enable an operator to select analysis options, view collected EM log data, view analysis results, and/or perform other tasks.

FIG. 1B illustrates a wireline logging environment in which an EM logging tool 40 is positioned within production tubing string 84 and casing string 72. In FIG. 1B, the EM logging tool 40 is suspended in borehole 16 that penetrates formations 19 of the earth 18. For example, the EM logging tool 40 may be suspended by a cable 15 having conductors and/or optical fibers for conveying power to the EM logging tool 40. The cable 15 may also be used as a communication interface for uphole and/or downhole communications. In at least some embodiments, the cable 15 wraps and unwraps as needed around cable reel 54 when lowering or raising the EM logging tool 40. As shown, the cable reel 54 may be part of a movable logging facility or vehicle 50 having a cable guide 52.

The EM logging tool 40 may include stabilizers 42 on one or more ends (e.g. opposite ends) of main body 41 to centralize the tool 40 within the production tubing string 84. The main body 41 of the EM logging tool 40 includes control electronics 44, transmitter(s) 46, and receiver(s) 48. In operation, transmitter(s) 46 are directed by the control electronics 44 to generate a time-varying EM field whose flux is guided by the production tubing string 84 and/or casing string 72. The flux induces a voltage in receiver(s) 48. The flux guide provided by the production tubing string 84 and/or casing string 72 is lossy due to induced eddy currents. The control electronics 44 store the voltages recorded by receiver(s) 48 to form an EM data log, which may be correlated with geometrical, electrical, and/or magnetic attributes of the production tubing string 84 and/or casing string 72. Corrosion of the production tubing string 84 and/or casing string 72 affects their geometrical, electrical, and/or magnetic attributes and can therefore be estimated from analysis of the EM log data. The control electronics 44 may also include a communication interface to transmit the EM data log to earth's surface. Additionally or alternatively, the EM data log obtained by the EM logging tool 40 can be stored and accessed later once the tool 40 reaches earth's surface.

At earth's surface, the surface interface 14 receives the EM data log via the cable 15 and conveys the EM field measurements to a computer system 20. Again, the interface 14 and/or computer system 20 (e.g., part of the movable logging facility or vehicle 50) may perform various operations such as converting signals from one format to another, storing the EM log data, and/or analyzing the EM log data to determine casing string attributes.

Figure 2A:
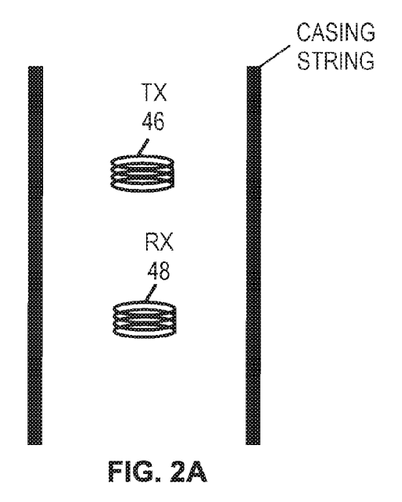
FIGS. 2A and 2B show illustrative transmitter/receiver configurations for an EM logging tool for multi-string corrosion monitoring.
Figure 2B:
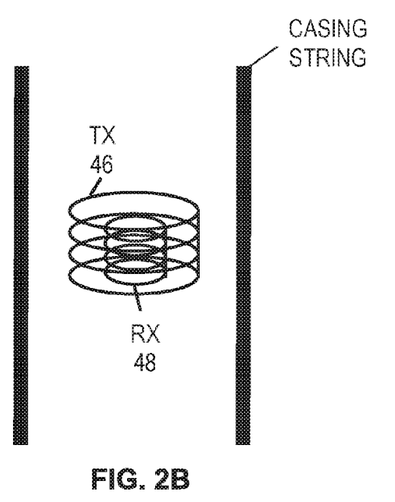

FIGS. 2A and 2B show illustrative transmitter/receiver configurations for an EM logging tool (e.g., tool 40). In FIG. 2A, transmitter 46 and receiver 48 are positioned within a casing string (e.g., strings 72 or 84) and are separated. Meanwhile, in FIG. 2B, transmitter 46 and receiver 48 are positioned within a casing string (e.g., strings 72 or 84) and are collocated. For example, transmitter 46 and receiver 48 may correspond to coils or solenoids, where the receiver 48 is positioned inside the transmitter 46, or vice versa. While only one transmitter 46 and one receiver 48 are shown in FIGS. 2A and 2B it should be understood, that EM logging tools such as tool 40 may have a plurality of sensor arrays, where the distance between transmitters 46 and receivers 48 for different sensor arrays may vary. Further, the dimensions of the transmitters 46 and receivers 48 may vary for different sensor arrays. Further, the operation of each sensor array may be varied by frequency-domain or time-domain adjustments.

Figure 3:
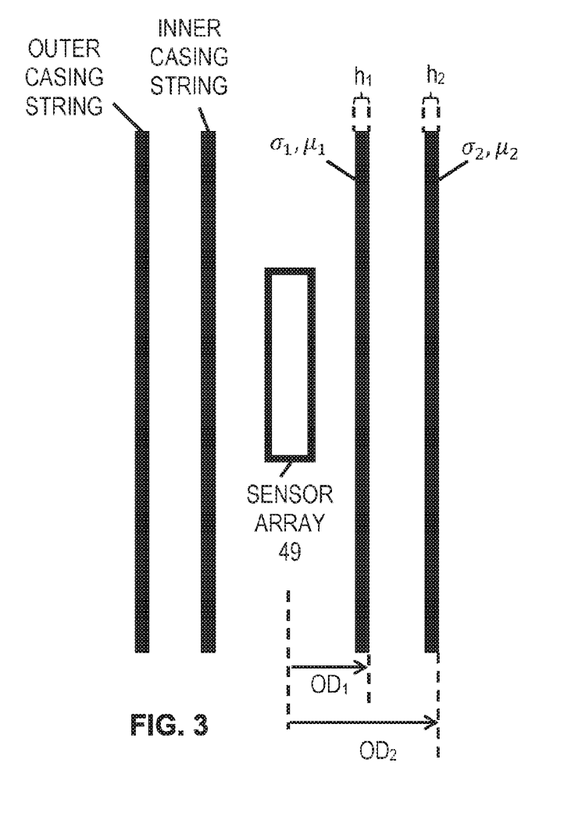
FIG. 3 shows a multi-string model with related attributes.

FIG. 3 shows a multi-string model with related attributes. In FIG. 3, a sensor array 49 (e.g., one or more transmitter/receiver arrays) is positioned within two casing strings (inner and outer casing strings). The sensing array 49 may be part of an EM logging tool such as tool 40 to enable various attributes of the inner and outer casing strings to be estimated. In the example multi-string scenarios of FIGS. 1A and 1B, the casing string 72 is an outer casing string, while the production tubing string 84 is an inner casing string.

One-dimensional (1D) forward and inversion models may be used to calculate multi-string casing thickness/corrosion attributes. For the two-string casing model of FIG. 3, casing thickness parameters are assumed to uniform along the axial direction. If casing materials are known, the attributes to be determined for the inner casing string include outer diameter ($OD_1$), casing thickness ($h_1$), conductivity ($\sigma_1$), and permeability ($\mu_1$). Similarly, the attributes to be determined for the outer casing string include outer diameter ($OD_2$), casing thickness ($h_2$), conductivity ($\sigma_2$), and permeability ($\mu_2$).

To calculate the casing thickness, a numerical optimization (e.g., a Gauss-Newton method) may be employed. In such case, unknown parameters are adjusted until the misfit error between measurement data and predicted data (computed via forward modeling using estimated parameters) are sufficiently small. This goal can be achieved by iteratively solving a non-linear problem that minimizes the objective cost function:

$$C(X) = 1/2[\|e(X)\|^2], \qquad \text{Equation (1)}$$

where the residual factor is defined as:

$$e(X) = \begin{bmatrix} S_1(X) - m_1 \\ S_2(X) - m_2 \\ \vdots \\ S_j(X) - m_j \\ \vdots \\ S_M(X) - m_M \end{bmatrix}, \quad \text{Equation (2)}$$

where $S_j(X)$ is the modeled tool response corresponding to a particular value of casing attribute vector X. For a single casing string scenario, X=[OD; h; σ; μ]. If casing OD and casing material are known or predetermined, X is simply equal to casing thickness h, $m_j$ is the corresponding measured data, and ∥.∥ refers to the L2-norm. If the EM logging tool 40 is operated as a time-domain tool, measured data $m_j$ are usually selected time bins that may correspond to different casing string diameters. On the other hand, if the EM logging tool 40 is operated at a frequency or multiple frequencies, measured data $m_j$ are collected signals at the frequency or frequencies used. If multiple sensor arrays are employed in the EM logging tool 40, measured data $m_j$ are tool responses (frequency or time-domain) from all of the selected arrays.

The above scheme corresponding to Equations 1 and 2 can be implemented straightforwardly by using classical optimization methods. However, it becomes inefficient when the optimization problem is relatively large such as when dealing with a multi-string scenario. Mathematically, as more unknowns are introduced into the inversion model, the final results become more unstable.

Observed from simulation results and theory of EM wave propagation, shorter sensor arrays with higher frequency (or with an earlier time channel) are more sensitive to an inner casing string (e.g., production tubing string 84). On the other hand, longer sensor arrays with lower frequency (or with a later time channel) are sensitive to both inner and outer strings (e.g., both production tubing string 84 and casing string 72). These behaviors enable calculation of inner string attributes using a simplified inversion model without taking the outer string into account. After estimating the inner string attributes, the outer string attributes can be computed afterwards in different ways. Two different approaches are described hereafter. These so-called multi-stage approaches can provide more accurate and rigorous results for multi-string monitoring operations.

General Multi-Stage Inversion Scheme

A general multi-stage inversion scheme (an N-string casing model is assumed) is proposed (operations A1 to A8) to provide accurate estimation of multi-string attributes as follows:

A1. Collect logging data.
A2. Start from the first logging position.
A3. Start with the nominal casing string parameters for all N pipes.
A4. For the $n^{th}$ pipe of a total of N pipes, where n=1 . . . N:
A5. For the $i^{th}$ attribute set of a total of I attribute sets, where i=1 . . . I. Each attribute set is a combination of X=[$OD_n$], X=[$h_n$], X=[$σ_n$], or X=[$μ_n$]
  a. PICK 1 of 2 OPTIONS
    i. Assume pipe in attributes in the $i^{th}$ attribute set are nominal where m>n.
    ii. Assume pipe m doesn't exist where m>n.
  b. PICK 1 of 3 OPTIONS:
    i. Assume pipe m attributes in the $i^{th}$ attribute set are nominal where m<n.
    ii. Assume pipe m attributes in $i^{th}$ attribute set are as solved in operation A4 before where m<n.
    iii. Assume pipe in doesn't exist where m<n.
  c. Solve for pipe n attributes in parameter set.
  d. Only use sensor arrays with lower or equal frequency compared to that used for pipe n−1 (n>1).
  e. Only use sensor arrays with longer or equal length compared to that used for pipe n−1 (n>1).
A6. PICK 1 of 2 OPTIONS
  a. Refine all casing string parameters n=1 . . . N.
    i. Raw data collected at longer sensor array with lower frequency (or later time channel) are used in the inversion model, which can be defined by Equations (1) and (2).
    ii. The inversion problem is a model with N casing strings.
    iii. The unknowns to be solved are: X=[$OD_1$, . . . , $_N$; $h_1$, . . . , $_N$; $σ_1$, . . . , $_N$; $μ_1$, . . . , $_N$].
    iv. Results from operation A4 are taken as initial values of unknowns.
  b. Iterate operations A4 and A5 until a desired iteration count is reached.
A7. Determine if all logging positions have been processed. If yes, go to the next operation. Otherwise, move to the next logging position and go back to operation A3.
A8. Finish.

Two-String Inversion Scheme

For a two-string casing model, the following example inversion scheme (operations B1 to B7) is proposed:

B1. Collect logging data.
B2. Start from the first logging position.
B3. Calculate $1^{st}$ casing string attributes only.
  a. Only raw data collected at shorter sensor array with higher frequency (or earlier time channel) are used in the inversion model, which can be defined by Equations (1) and (2).
  b. The inversion problem is either a model with only $1^{st}$ casing-string or a model with $1^{st}$ casing-string and nominal $2^{nd}$ casing-string attributes.
  c. The unknowns to be solved are: X=[$OD_1$; $h_1$; $σ_1$; $μ_1$].
B4. Calculate $2^{nd}$ casing string attributes only.
  a. Only raw data collected at longer sensor array with lower frequency (or later time channel) are used in the inversion model, which can be defined by Equations (1) and (2).
  b. The inversion problem is a model with two casing strings, where the $1^{st}$ casing-string attributes are computed from operation B3.
  c. The unknowns to be solved are: X=[$OD_2$; $h_2$; $σ_2$; $μ_2$].
B5. Refine $1^{st}$ and $2^{nd}$ casing string attributes.
  a. Raw data collected at longer sensor array with lower frequency (or later time channel) are used in the inversion model, which can be defined by Equations (1) and (2).
  b. The inversion problem is a model with two casing strings.
  c. The unknowns to be solved are: X=[$OD_{1,2}$; $h_{1,2}$; $σ_{1,2}$; $μ_{1,2}$]
  d. Results from operations B3 and B4 are taken as initial values of unknowns.
B6. Determine if all logging positions have been processed. If yes, go to the next operation.
Otherwise, move to the next logging position and go back to operation B3.

B7. Finish.

Figure 4A:
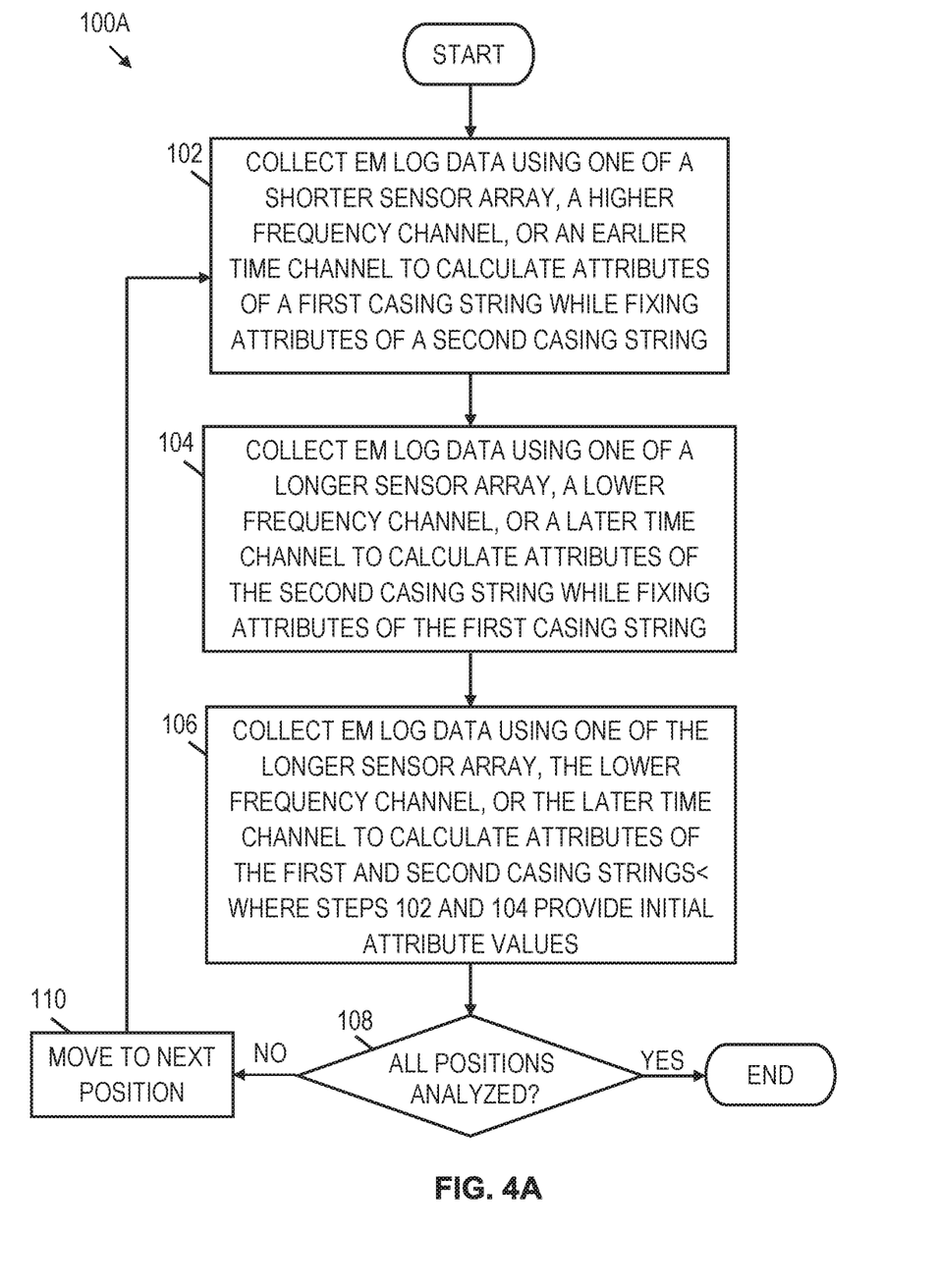
FIGS. 4A and 4B show illustrative flowcharts for multi-string corrosion monitoring methods.

FIG. 4A shows an illustrative flowchart for a multi-string monitoring method 100A related to the above two-string inversion scheme. The method 100A assumes a two-string arrangement with inner and outer strings, and an EM logging tool 40 with multiple sensor arrays (each having a different length), multiple frequency channels, or multiple time channels. As shown, the method 100 includes collecting EM log data using one of a shorter sensor array (compared to other sensor array options), a higher frequency channel (compared to other frequency channel options), or an earlier time channel (compared to other time channel options) to calculate attributes of a first casing string while fixing attributes of a second casing string (block 102). The fixed attributes for the second casing string may correspond to null values (as if there were no second casing string) or nominal values (as if the second casing string does not significantly affect the EM log data). As an example, for block 102, the attributes for the inner casing string are the unknowns, while the attributes of the outer casing string are known.

At block 104, EM log data is collected using one of a longer sensor array (compared to other sensor array options), a lower frequency channel (compared to other frequency channel options), or a later time channel (compared to other time channel options) to calculate attributes of a second casing string while fixing attributes of a first casing string. As an example, for block 104, the attributes for the outer casing string are the unknowns, while the attributes of the inner casing string are known. At block 106, EM log data is collected using one of the longer sensor array, the lower frequency channel, or the later time channel to calculate attributes of the first and second casing strings, where the attributes calculated at blocks 102 and 104 are used as the initial values for unknown attributes to be calculated at block 106. For block 106, the attributes of the inner and outer casing strings are the unknowns, and are calculated in part by using the attribute values determined in blocks 102 and 104 as the initial values for the calculations of block 106. If all logging positions have been analyzed (decision block 108), the method 100A ends. Otherwise, the method 100A moves to a next logging position at block 110, and blocks 102, 104, 106, and 108 are repeated.

Alternative Inversion Scheme

An alternative inversion scheme can be derived from the previous two-string inversion scheme. Compared to the previous inversion scheme, only attributes of either the inner casing string or the outer casing string are accounted for. This alternative inversion scheme (operations C1 to C7) assumes a two-string casing model and is given as follows:

C1. Collect logging data.

C2. Start from the first logging position.

C3. Calculate $1^{st}$ casing string attributes only.
  a. Only raw data collected at shorter sensor array with higher frequency (or earlier time channel) are used in the inversion model, which can be defined by Equations (1) and (2).
  b. The inversion problem is either a model with only $1^{st}$ casing-string or a model with $1^{st}$ casing-string and nominal $2^{nd}$ casing-string attributes.
  c. The unknowns to be solved are: $X=[OD_1; h_1; \sigma_1; \mu_1]$.
  d. If this operation is called after operation C5, results from operation C4 are taken as initial values of unknowns.

C4. Calculate $2^{nd}$ casing string attributes only.
  a. Only raw data collected at longer sensor array with lower frequency (or later time channel) are used in the inversion model, which can be defined by Equations (1) and (2).
  b. The inversion problem is a model with two casing strings, where the $1^{st}$ casing-string parameters are computed from operation C3.
  c. The unknowns to be solved are: $X=[OD_2; h_2; \sigma_2; \mu_2]$.

C5. If additional iteration is desired, then go to operation C3. Otherwise, go to the next operation.
  a. Since this scheme does not compute multi-string casing attributes simultaneously, its accuracy may not good as the previous scheme. To address this potential issue, additional iterations can be utilized to improve its accuracy, by further refining computed casing attributes.

C6. Determine if all logging positions have been processed. If yes, go to the next operation. Otherwise, move to the next logging position and go back to operation C3.

C7. Finish.

Figure 4B:
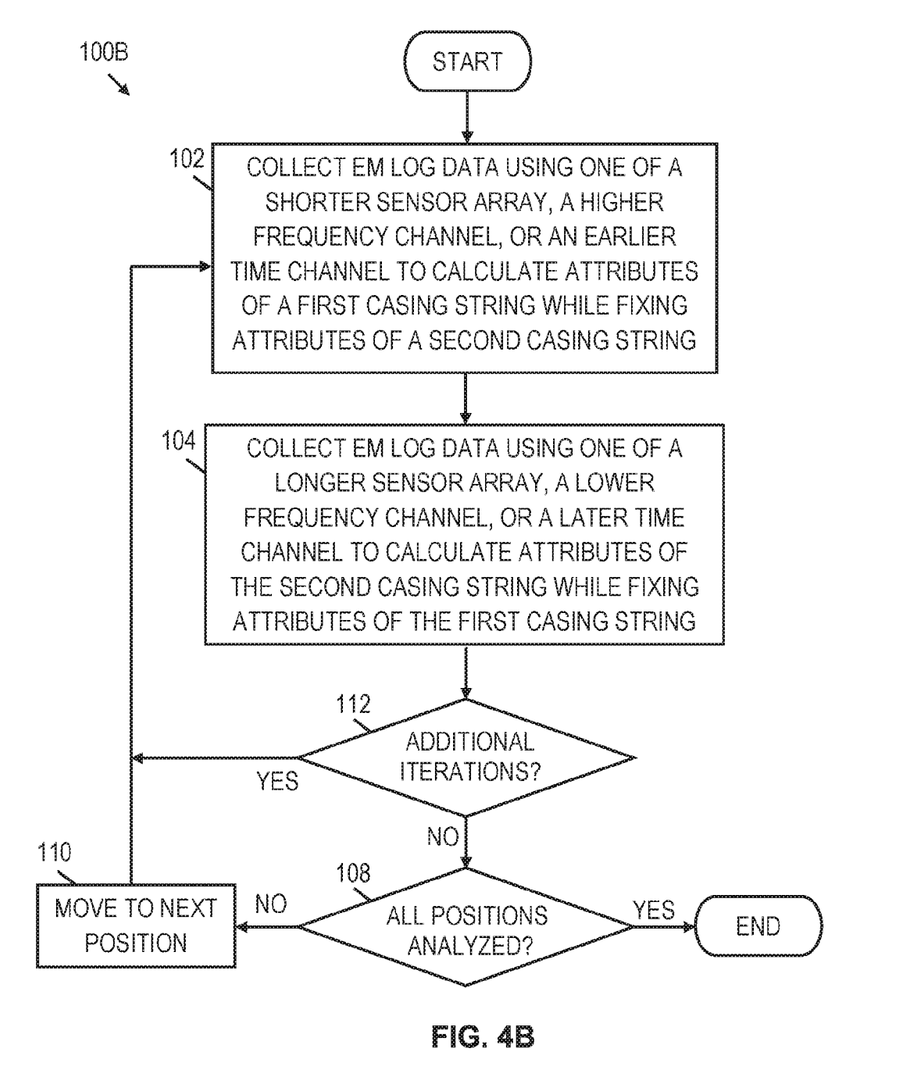

FIG. 4B shows an illustrative flowchart for a multi-string monitoring method 100B related to the alternative two-string inversion scheme described above. In method 100B, block 102 and 104 are the same as described for method 100A. After block 104, a decision is made regarding whether to perform additional iterations (decision block 112). For example, the decision to perform additional iterations may be based on an accuracy threshold or a number of iterations threshold. If additional iterations are to be performed (decision block 112), the method 100B returns to blocks 102 and 104, where the attribute values determined in the previous iteration are used as the fixed attribute values for the respective blocks. If no additional iterations are to be performed (decision block 112), the method 100B proceeds to decision block 108. If all logging positions have been analyzed (decision block 108), the method 100B ends. Otherwise, the method 100B moves to a next logging position at block 110, and blocks 102, 104, 112, and 108 are repeated.

Multi-level Multi-stage scheme.

For the two-string inversion options described above, casing string parameters may be computed at different levels or sub-stages of the stages described herein. Assuming the OD value is known, at least three casing string attributes (h, $\sigma$, $\mu$) need to be solved for each casing string. For example, block 102 may solve for h, $\sigma$, $\mu$ of a first casing string, block 104 may solve for h, $\sigma$, $\mu$ of a second casing string, and so on. Rather than solve for all three of the example attributes h, $\sigma$, $\mu$ in a single operation, a multi-level inversion can be applied for each of the blocks 102 and 104. In such case, blocks 102 and 104 would be further divided into multiple levels. For example, each of blocks 102 and 104 could be divided into two or three levels to determine the three example attributes (h, $\sigma$, $\mu$).

Figure 5A:
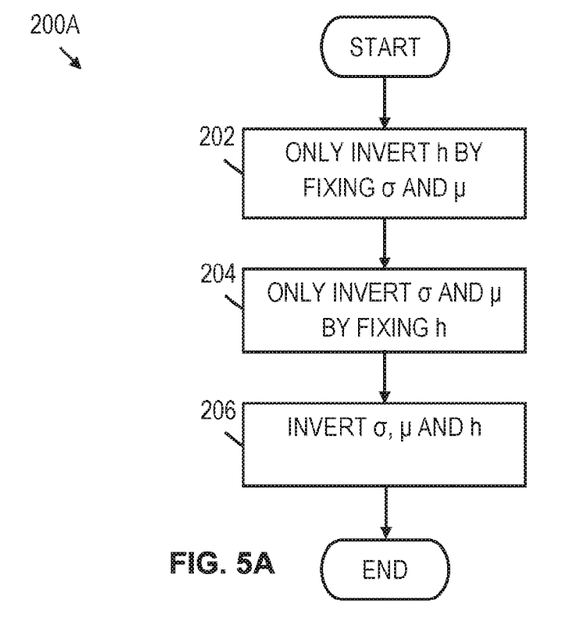
FIGS. 5A and 5B show illustrative flowcharts for multi-stage inversion methods related to multi-string corrosion monitoring.
Figure 5B:
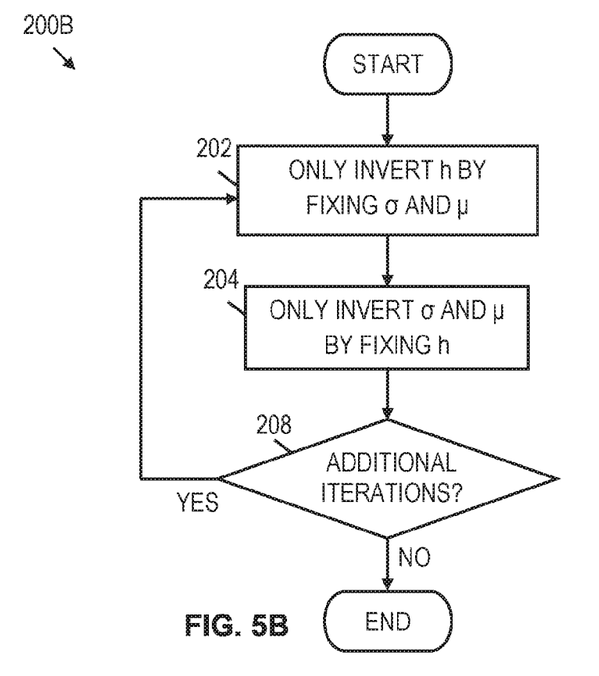

FIGS. 5A and 5B show illustrative flowcharts for multi-level inversion methods 200A and 200B. For example, the methods 200A and 200B may be employed for each of the blocks 102, 104, and 106 described previously for methods 100A and 100B. In method 200A, only h is inverted by fixing the values for $\sigma$ and $\mu$ (block 202). At block 204, $\sigma$ and $\mu$ are inverted by fixing the value for h. At block 206, an inversion for h, $\sigma$, $\mu$ is performed, where the values determined at block 202 and 204 are used as the initial values for h, $\sigma$, $\mu$.

In method 200B, blocks 202 and 204 are the same as method 200C. After block 204, a decision is made regarding whether to perform additional iterations (decision block 208). For example, the decision to perform additional iterations may be based on an accuracy threshold or a number of iterations threshold. If additional iterations are to be performed (decision block 208), the method 200B returns to block 202 and 204, where the attribute values determined in the previous iteration are used as the fixed attribute values for the respective blocks. If no additional iterations are to be performed (decision block 208), the method 200B ends.

In alternative embodiments, multi-level inversions may vary from methods 200A and 200B. In general, a multi-level inversion includes multiple levels, where a different attribute or set of attributes is inverted for each level while other attributes are fixed. The example attributes given herein include h, σ, and μ. In methods 200A and 200B, h is inverted in a first level (block 202), while σ and μ are inverted in a second level (block 204). In alternative embodiments, σ and μ may be inverted in separate staged. Further, σ and/or μ may be inverted before h.

Embodiments disclosed herein include:

A: A multi-string monitoring method that comprises inverting based on a first set of EM log data to determine attributes of a first casing string while attributes of a second casing string are assigned a fixed value, and inverting based on a second set of EM log data to determine attributes of a second casing string while attributes of the first casing string are assigned a fixed value.

B: A multi-string monitoring system that comprises an EM logging tool positioned within first and second casing strings to collect at least first and second sets of EM log data, and a processing unit in communication with EM logging tool. The processing unit calculates attributes of the first casing string based on the first set of EM log data while attributes of the second casing string are assigned a fixed value, and calculates attributes of the second casing string based on the second set of EM log data while attributes of the first casing string are assigned a fixed value.

Each of the embodiments, A and B, may have one or more of the following additional elements in any combination. Element 1: further comprising the attributes include at least one of a casing thickness, a casing conductivity, and a casing permeability. Element 2: further comprising collecting the first set of EM log data using a first sensor array, and collecting the second set of EM log data using a second sensor array that is longer than the first sensor array. Element 3: further comprising collecting the first set of EM log data using a first frequency channel, and collecting the second set of EM log data using a second frequency channel that is lower than the first frequency channel. Element 4: further comprising collecting the first set of EM log data using a first time channel, and collecting the second set of EM log data using a second time channel that is later than the first time channel. Element 5: further comprising repeating the inverting operations for each of a plurality of positions along the multi-string. Element 6: further comprising repeating the inverting operations for each of a plurality of iterations until a threshold quality or threshold number of iterations is reached. Element 7: further comprising inverting to determine attributes of both the first and second casing strings, where initial values for the attributes to be determined are obtained from previous inverting operations. Element 8: further comprising performing a multi-stage inversion to calculate attributes of the first or second casing strings, the multi-stage inversion including multiple stages, where a different casing string attribute or set of casing string attributes is inverted for each stage while at least one other casing string attribute is fixed. Element 9: the multi-stage inversion comprises a first stage that inverts a casing thickness attribute based on a fixed casing conductivity attribute and fixed casing permeability attribute. Element 10: the multi-stage inversion comprises a second stage that inverts a casing conductivity attribute and a casing permeability attribute based on a fixed casing thickness attribute. Element 11: further comprising performing multiple iterations of the multi-stage inversion to calculate attributes of at least one of the first and second casing strings until a threshold quality or threshold number of iterations is reached.

Element 12: the EM logging tool collects the first set of EM log data using a first sensor array, and collects the second set of EM log data using a second sensor array that is longer than the first sensor array. Element 13: the EM logging tool collects the first set of EM log data using a first frequency channel, and collects the second set of EM log data using a second frequency channel that is lower than the first frequency channel. Element 14: the EM logging tool collects the first set of EM log data using a first time channel, and collects the second set of EM log data using a second time channel that is later than the first time channel. Element 15: the processing unit calculates attributes of at least one of the first and second casing strings for each of a plurality of iterations until a threshold quality or threshold number of iterations is reached. Element 16: the processing unit re-calculates attributes of the first and second casing strings based on the calculated attributes of the first and second casing strings. Element 17: the processing unit performs a multi-stage inversion to calculate attributes of the first or second casing strings, wherein the multi-stage inversion includes multiple levels, where a different casing string attribute or set of casing string attributes is inverted for each level while at least one other casing string attribute is fixed. Element 18: the multi-stage inversion comprises a first level that inverts a casing thickness attribute based on a fixed casing conductivity attribute and fixed casing permeability attribute, and wherein the multi-stage inversion comprises a second level that inverts a casing conductivity attribute and a casing permeability attribute based on a fixed casing thickness attribute.

Numerous other variations and modifications will become apparent to those skilled in the art once the above disclosure is fully appreciated. For example, the disclosed two-string inversion schemes can be extended to three-string, four-string, or other multi-string scenarios as needed. Further, in some embodiments, the order of the processing operations described herein may vary and/or be performed in parallel. It is intended that the following claims be interpreted to embrace all such variations and modifications where applicable.

What is claimed is:

1. A multi-string corrosion monitoring method that comprises:
   disposing an electromagnetic (EM) logging tool downhole;
   generating a time-varying EM field along a casing string with a transmitter, wherein the transmitter is a coil or a solenoid;
   energizing a first casing string, wherein an eddy current is formed in the first casing string;
   recording a voltage induced by the EM field with a receiver, wherein the receiver is a coil or a solenoid;
   inverting based on a first set of electromagnetic (EM) log data to determine attributes of the first casing string while attributes of a second casing string are assigned a fixed value;

inverting based on a second set of EM log data to determine attributes of a second casing string while attributes of the first casing string are assigned a fixed value;

collecting the first set of EM log data using a first sensor array; and collecting the second set of EM log data using a second sensor array that is longer than the first sensor array.

2. The method of claim 1, wherein the attributes include at least one of a casing thickness, a casing conductivity, and a casing permeability.

3. The method of claim 1, further comprising:
collecting the first set of EM log data using a first frequency channel; and
collecting the second set of EM log data using a second frequency channel that is lower than the first frequency channel.

4. The method of claim 1, further comprising:
collecting the first set of EM log data using a first time channel; and
collecting the second set of EM log data using a second time channel that is later than the first time channel.

5. The method of claim 1, further comprising repeating the inverting operations for each of a plurality of positions along the multi-string.

6. The method of claim 1, further comprising repeating the inverting operations for each of a plurality of iterations until a threshold quality or threshold number of iterations is reached.

7. The method of claim 1, further comprising inverting to determine attributes of both the first and second casing strings, where initial values for the attributes to be determined are obtained from previous inverting operations.

8. The method of claim 1, further comprising performing a multi-stage inversion to calculate attributes of the first or second casing strings, the multi-stage inversion including multiple stages, where a different casing string attribute or set of casing strings attributes is inverted for each stage while at least one other casing string attribute is fixed.

9. The method of claim 8, wherein the multi-stage inversion comprises a first stage that inverts a casing thickness attribute based on a fixed casing conductivity attribute and fixed casing permeability attribute.

10. The method of claim 8, wherein the multi-stage inversion comprises a second stage that inverts a casing conductivity attribute and a casing permeability attribute based on a fixed casing thickness attribute.

11. The method of claim 8, further comprising performing multiple iterations of the multi-stage inversion to calculate attributes of at least one of the first and second casing strings until a threshold quality or threshold number of iterations is reached.

12. A multi-string corrosion monitoring system that comprises:
an electromagnetic (EM) logging tool positioned within first and second casing strings to collect at least first and second sets of EM log data, wherein the EM logging tool comprises:
a transmitter, wherein the transmitter generates a time-varying EM field, wherein the transmitter is a coil or a solenoid; and
a receiver, wherein the receiver records a voltage induced by the EM field, wherein the receiver is a coil or a solenoid; and
a processing unit in communication with EM logging tool, wherein the processing unit
calculates attributes of the first casing string based on the first set of EM log data while attributes of the second casing string are assigned a fixed value, and
calculates attributes of the second casing string based on the second set of EM log data while attributes of the first casing string are assigned a fixed value, wherein the EM logging tool collects the first set of EM log data using a first sensor array, and collects the second set of EM log data using a second sensor array that is longer than the first sensor array.

13. The system of claim 12, wherein the EM logging tool collects the first set of EM log data using a first frequency channel, and collects the second set of EM log data using a second frequency channel that is lower than the first frequency channel.

14. The system of claim 12, wherein the EM logging tool collects the first set of EM log data using a first time channel, and collects the second set of EM log data using a second time channel that is later than the first time channel.

15. The system of claim 12, wherein the processing unit calculates attributes of at least one of the first and second casing strings for each of a plurality of iterations until a threshold quality or threshold number of iterations is reached.

16. The system of claim 12, wherein the processing unit re-calculates attributes of the first and second casing strings based on the calculated attributes of the first and second casing strings.

17. The system of claim 12, wherein the processing unit performs a multi-stage inversion to calculate attributes of the first or second casing strings, wherein the multi-stage inversion includes multiple levels, where a different casing string attribute or set of casing string attributes is inverted for each level while at least one other casing string attribute is fixed.

18. The system of claim 17, wherein the multi-stage inversion comprises a first level that inverts a casing thickness attribute based on a fixed casing conductivity attribute and fixed casing permeability attribute, and wherein the multi-stage inversion comprises a second level that inverts a casing conductivity attribute and a casing permeability attribute based on a fixed casing thickness attribute.

19. A multi-string corrosion monitoring system that comprises:
an electromagnetic (EM) logging tool positioned within first and second casing strings to collect at least first and second sets of EM log data, wherein the EM logging tool comprises:
a transmitter, wherein the transmitter generates a time-varying EM field, wherein the transmitter is a coil or a solenoid; and
a receiver, wherein the receiver records a voltage induced by the EM field, wherein the receiver is a coil or a solenoid, and wherein the receiver is configured to record the first set of EM log data on a first frequency channel and the seconds set of EM log data on the second frequency channel that is lower than the first frequency channel; and
a processing unit in communication with EM logging tool, wherein the processing unit
calculates attributes of the first casing string based on the first set of EM log data while attributes of the second casing string are assigned a fixed value, and
calculates attributes of the second casing string based on the second set of EM log data while attributes of the first casing string are assigned a fixed value, wherein the EM logging tool collects the first set of EM log data using a first sensor array, and collects the second set of EM log data using a second sensor array that is longer than the first sensor array.

* * * * *